United States Patent [19]

Kaiser et al.

[11] 4,195,154
[45] Mar. 25, 1980

[54] NOVEL 2-AMIDO- OR 2-AMINO-ALKYL ETHERS OF POLYHYDRIC POLYPHENOLS AND PROCESS FOR PREPARING SAME

[75] Inventors: Mark E. Kaiser; Harry A. Smith, both of Midland, Mich.

[73] Assignee: The Dow Chemical Company, Midland, Mich.

[21] Appl. No.: 824,768

[22] Filed: Aug. 15, 1977

[51] Int. Cl.² .................. C08G 59/50; C07C 87/28; C07C 103/38
[52] U.S. Cl. .................. 528/98; 260/570.5 P; 260/570.5 S; 260/559 R; 260/558 S; 424/330; 528/99; 528/332; 525/504; 525/534; 525/497
[58] Field of Search .................. 260/570.5 P, 559 R, 260/59 R, 47 EN, 830 R; 528/132, 98, 99

[56] References Cited

U.S. PATENT DOCUMENTS

| | | | |
|---|---|---|---|
| 3,461,099 | 8/1969 | Muzyczko et al. | 260/59 |
| 3,544,517 | 12/1970 | Muzyczko et al. | 260/47 |
| 3,654,229 | 4/1972 | Hunsucker | 260/67.6 R |

FOREIGN PATENT DOCUMENTS 1062253 7/1959 Fed. Rep. of Germany .
2303304 8/1973 Fed. Rep. of Germany .

Primary Examiner—Earl A. Nielsen
Attorney, Agent, or Firm—L. Wayne White; Michael L. Glenn

[57] ABSTRACT

The title compounds are of the formula:

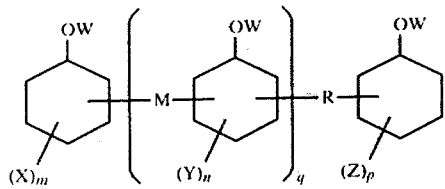

wherein R is a chemical bond, oxygen, sulfur, alkylene or alkylidene; W is hydrogen or a ($-CR_1R_2-CR_3R_4-NHR_5$) group with the proviso that at least two W groups are ($-CH_1R_2-CR_3R_4-NHR_5$) groups; wherein $R_1-R_4$ are each independently hydrogen, lower alkyl or hydroxy-substituted lower alkyl; $R_5$ is hydrogen or a

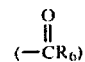

group, wherein $R_6$ is hydrogen, hydrocarbyl or inertly substituted hydrocarbyl; X, Y and Z are each independently inert substituents; m and p are each independently integers of from zero to four, inclusive; n is an integer of from zero to three, inclusive; q is a number of from zero to about ten; and M is alkylene or alkylidene. They are conveniently prepared by reacting a 2-oxazoline of the formula:

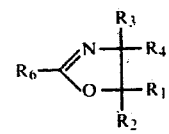

with a polyhydric polyphenol of the formula:

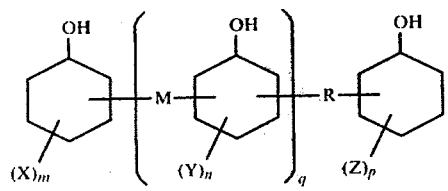

in the presence of certain metal salt catalysts (e.g. zinc acetate).

13 Claims, No Drawings

NOVEL 2-AMIDO- OR 2-AMINO-ALKYL ETHERS OF POLYHYDRIC POLYPHENOLS AND PROCESS FOR PREPARING SAME

BACKGROUND OF THE INVENTION

1. Field of the Invention

This invention pertains to a novel class of 2-amido- or 2-aminoalkyl ethers of polyhydric polyphenols and a method of preparation.

2. Prior Art

The reaction of oxazolines and mono-hydric phenols has been investigated to a limited extent. John A. Frump, *Chemical Reviews*, Vol. 71, No. 5 (1971) at page 497 states that substituted 2-oxazolines react with phenol in the absence of water to give ethers and carboxamides.

W. Seeliger et al., *Agnew. Chem. Internat. Edit.*, Vol. 5, No. 10 (1966) at page 878, teach that cyclic imidic esters and phenols react most often to produce 2- or 3-substituted N-alkyl amide derivatives, although 2-aminoethyl or 3-aminopropyl esters of carboxylic acids or their derivatives occasionally result.

In German Pat. No. 1,062,253, A. Jäger describes the preparation of various ether and carboxamide compounds by treating certain substituted oxazolines with certain phenols, with the exclusion of water. A mixture of phenol and 2-phenyloxazoline refluxed for 7 hours yielded PhCONHCH$_2$CH$_2$OPh as a product. Similarly, p-bis(oxazolinyl)benzene and phenol gave N,N'-bis($\beta$-phenoxyethyl)terephthalamide. Finally, Jäger found that a mixture of 2-phenyl-2-oxazoline and hydroquinone produced 1,4-bis($\beta$-benzamidoethoxy)benzene.

Attempts have also been made to prepare 2-aminoalkyl ethers of phenol by reacting ethylenimine (aziridine) or a C-substituted ethylenimine with phenol. Cf. Dermer and Ham, "Ethylenimine and Other Aziridines" (1969) at page 226. However, such reactions lead to mixed products, mainly polymeric ethylenimine derivatives.

None of the reaction products set forth above contained the polyhydric polyphenol structures of the instant compounds, nor was there any evidence to suggest the high yields common to the instant process. The prior art is void, insofar as we are aware, of any attempts to prepare the amides or amines of polyhydric polyphenols.

SUMMARY OF THE INVENTION

We have discovered a novel class of 2-amido- and 2-aminoalkyl ethers of polyhydric polyphenols and a novel process for preparing same.

The novel compounds correspond to the formula:

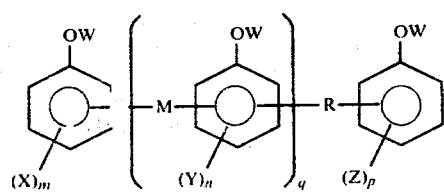

wherein R is a chemical bond, oxygen, sulfur, alkylene or alkylidene; W is hydrogen or a (—CR$_1$R$_2$—CR$_3$R$_4$—NHR$_5$) group with the proviso that at least two W groups are (—CR$_1$R$_2$—CR$_3$R$_4$—NHR$_5$) groups; wherein R$_1$-R$_4$ are each independently hydrogen, lower alkyl or hydroxy-substituted lower alkyl; R$_5$ is hydrogen or a

group, wherein R$_6$ is hydrogen, hydrocarbyl or inertly substituted hydrocarbyl; X, Y and Z are each independently inert substituents; m and p are each indepedently integers of from zero to four, inclusive; n is an integer of from zero to three, inclusive; q is a number of from zero to about ten; and M is alkylene or alkylidene. By "inertly-substituted hydrocarbyl" is meant a hydrocarbyl group bearing a substituent(s) that is inert in the process of making the compounds, as hereafter described. Likewise, "inert substituent" as applied to X, Y and Z denotes substituents which are inert in the process of making the compounds.

The novel process comprises reacting by contacting a 2-oxazoline with a polyhydric polyphenol in the presence of a small but catalytic amount of at least one transition metal or tin salt catalyst, said transition metal salt catalyst being a salt of a metal in groups 1b, 2b, 6b, 7b and 8 which is included in rows 4 and 5 of the Periodic Table of the Elements, inclusive, to thereby produce an amide of the formula:

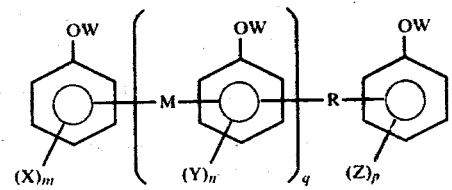

wherein W, X, Y, Z, etc. have the aforesaid meanings and R$_5$ is a

group. The free amine (R$_5$=H) is prepared by reacting the amide thus obtained with acid or base so as to effect hydrolysis.

DETAILED DESCRIPTION OF THE INVENTION

The instant reaction may be illustrated as follows:

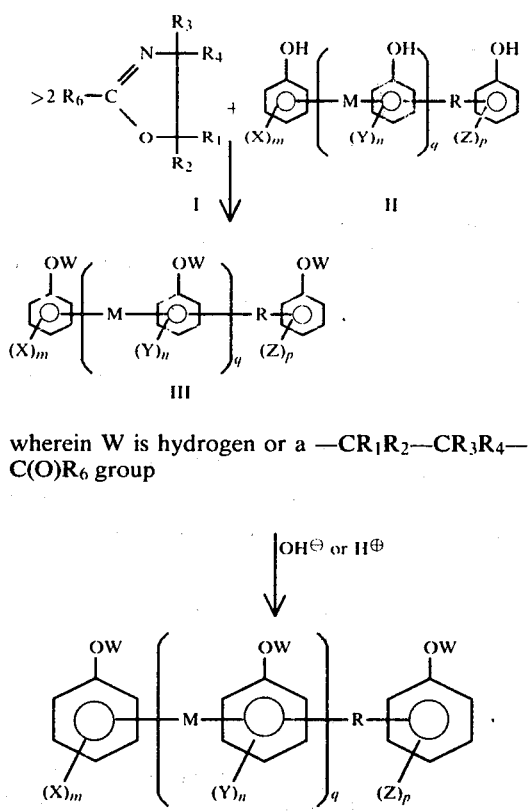

wherein W is hydrogen or a —CR$_1$R$_2$—CR$_3$R$_4$—NH-C(O)R$_6$ group wherein W is hydrogen or a —CR$_1$R$_2$—CR$_3$R$_4$—NH$_2$ group. In formulas I-IV:

R is preferably alkylene or alkylidene of from one to four carbon atoms, inclusive, and more preferably methylene or isopropylidene.

R$_1$ and R$_2$ are preferably hydrogen and R$_3$ and R$_4$ are preferably hydrogen or methyl. More preferably, R$_1$-R$_4$ are each hydrogen.

R$_6$ is preferably hydrogen or alkyl of from 1 to about 17 carbon atoms, inclusive, and more preferably methyl or ethyl.

M is preferably lower alkylene and more preferably methylene.

X, Y, and Z are preferably halogen, alkyl or alkoxy and more preferably bromine.

m and p are preferably zero or two and more preferably zero.

n is preferably zero or one and more preferably zero.

q is a number preferably from zero to six and more preferably zero.

The polyamides (III) ar normally colored, glassy resins or solids.

The Reactants

The 2-oxazoline reactants (I) are a well-known class of compounds which are typically prepared by cyclodehydration of an N-(2-hydroxyalkyl)carboxamide. Cf. Frump, supra, at page 484.

The oxazoline reactants are substituted in the 2-position with hydrogen, inert hydrocarbyl (e.g., aliphatic hydrocarbyl groups, such as alkyl, alkenyl, aralkyl, etc.; aromatic hydrocarbyl groups, such as aryl, alkaryl, etc.; alicyclic hydrocarbyl groups, such as cycloalkyl, cycloalkenyl, etc.; and the like), or inertly-substituted hydrocarbyl groups (e.g., hydrocarbyl groups bearing hydroxy, alkoxy, ester moieties, etc.). By inert it again is meant inert in the process. The oxazoline reactants are substituted in the 4- and/or 5-positions with hydrogen, lower alkyl (e.g., methyl, ethyl, propyl, isopropyl, etc.) or hydroxy-substituted lower alkyl (e.g., hydroxymethyl, hydroxyethyl, etc.). Any member of the known class of 2-oxazolines may be used herein. Thus, suitable 2-oxazolines include, for example, 2-oxazoline (i.e., 2-H-2-oxazoline), 4-methyl-2-oxazoline, 5-methyl-2-oxazoline, 4,5-dimethyl-2-oxazoline, 4,4-dimethyl-2-oxazoline, 2-hydroxymethylethyl-2-oxazoline, 4-hydroxymethyl-2-oxazoline, 2-ethyl-2-oxazoline, 2-ethyl-4-methyl-2-oxazoline, 2-ethyl-4,5-dimethyl-2-oxazoline, 2-cyclohexyl-2-oxazoline, 2-phenyl-2-oxazoline, 2-tolyl-2-oxazoline, 2-heptadecen-9-yl-2-oxazoline, and the like. 2-H- and 2-alkyl (C$_1$ to about C$_{17}$)-2-oxazolines are preferred and 2-methyl- and 2-ethyl-2-oxazoline are the most preferred reactants. The oxazolines substituted in the 4- and/or 5-positions generally react somewhat more slowly due to steric hindrance resulting from this substitution.

The polyhydric polyphenols (II) likewise form a known class of compounds having many members, any member of which can be used in the instant process. These compounds contain at least two aromatic rings joined by a chemical bond or a divalent radical of oxygen, sulfur or organic group as set forth above, and bearing at least one hydroxyl group per aromatic ring. Certain polyphenols are, however, widely marketed and are therefore the compounds of choice because of their availability; of these, bisphenol A (2,2-bis(4-hydroxyphenyl)propane), bisphenol F (2,2-bis(4-hyroxyphenyl)methane) and tetrabromobisphenol A (2,2-bis(4-hydroxy-ar,ar'-dibromophenyl)propane) are preferred. Examples of polyhydric polyphenols (II) include: the bisphenols (i.e., ar,ar'-dihydroxybiphenyl); novolacs with a hydroxyl functionality of at least two, such as bisphenol F; oxybisphenols (i.e., ar,ar'-dihydroxydiphenyl oxide); thiobisphenols (i.e., ar,ar'-dihydroxydiphenyl sulfide); and the like, and the corresponding compounds bearing halogen(s), alkyl (e.g., methyl, ethyl, butyl, etc.), and alkoxy groups, and the like. The novolacs used herein are conventionally referred to as phenol-aldehyde or phenol-ketone condensates. The substituents, if any, on the polyphenols are inert in the process as described below. The ring-substituted polyphenols of choice have identical substitution on each ring; most preferred within this category are those in which m and n in formulas II-IV are no greater than two.

The process for preparing the title compounds makes use of at least one tin or transition metal salt to catalyze the oxazoline-phenolic reaction. This catalyst is a salt of tin or a metal in groups 1b, 2b, 6b, 7b and 8 which is included in rows 4 and 5 of the Periodic Table of the Elements, inclusive, as shown on page B-3 of the "Handbook of Chemistry and Physics", 48th edit., Chemical Rubber Co. (1967). The catalyst is required in only small but catalytic amounts. Convenient reaction rates have been observed when the catalyst is present in amounts up to about 6.0 weight percent based on the reactants.

The catalysts include both organic and inorganic soluble salts of tin and such transition metals as chromium, manganese, iron, cobalt, nickel, copper, zinc, molybdenum, technitium, ruthenium, rhodium, palladium, silver and cadmium. By soluble is meant at least minimally soluble in the reaction mixture at reaction temperature (e.g., 100 parts per million). The anion portion of these salts can be varied to convenience. Suitable anions include, for example, acetate, acetylacetonate, octoate, oxalate, benzoate, naphthanate, fluoride, chloride, bromide, nitrate, sulfate, ammonium sulfate, potassium sulfate, ammonium citrate, phosphate, molybdate, tungstate, and the like. The preferred anions are acetate, sulfate and the halides. Suitable catalysts include, for example, zinc acetate, copper acetylacetonate, stannous octoate, cobalt oxalate, cadmium fluoride, rhodium trichloride, zinc bromide, iron chloride, zinc nitrate, silver sulfate, ferric ammonium sulfate, ferrous sulfate, ferrous phosphate, nickel molybdate, ferrous tungstate, stannous chloride, and the like. Many of these salts are prepared and marketed as hydrates and such hydrates are likewise suitable for use in the instant invention. The preferred catalysts are salts of zinc; and of these, zinc acetate is most preferred.

The stoichiometry of the reaction requires one mole of oxazoline reactant per phenolic hydroxyl group. We normally conduct the reaction using essentially stoichiometric quantities of reactants, with a slight excess of oxazoline reactant being preferred. The process is generally carried out with the reactants in the liquid phase and usually conducted neat, although it is convenient in the case of solid higher molecular weight polyphenols to first dissolve same in an inert organic solvent. By way of illustration, liquid aromatic hydrocarbons (e.g., toluene), alcohols (e.g., methanol, ethanol) and glycol ethers (e.g., diethylene glycol monoethyl ether) are appropriate solvents.

The polyamides (III) obtained by reacting a 2-oxazoline with a polyhydric polyphenol can be hydrolyzed with either acid or base to form the corresponding polyamines (IV). The rate of hydrolysis is lower using base but basic hydrolysis is preferred because of higher product purity and yield. The preferred acid and base are hydrochloric acid and sodium hydroxide. The polyamine (IV) produced by this hydrolysis can be isolated from the reaction mixture by solvent extraction using, for example, methylene chloride. Both the preparation of the polyamide and the hydrolysis are preferably carried out in an inert atmosphere, such as nitrogen.

The class of polyamines (IV) is a novel and versatile class of compounds, normally occurring as solids. Because of the free amine groups which are present, these polyamines behave similarly to other aliphatic polyamines and can be used in many of the same applications. They are excellent epoxy curing agents, acid scavengers, possess antimicrobial and antifungal activity and can be used in the preparation of various polyamides (i.e., nylons).

The following examples further illustrate the invention.

EXAMPLE 1

A mixture of 57 g (0.25 mole) of bisphenol A, 49.5 g (0.5 mole) of 2-ethyl-2-oxazoline and 0.5 g of zinc acetate dihydrate was purged with nitrogen and heated to reflux under a slow nitrogen stream. During refluxing for 2.5 hours starting at 170° C.–180° C., the temperature slowly increased to 210° C. where it was held for an additional 2.5 hours. Cooling yielded a pale orange, glassy solid found to be neutral when dissolved in a 50/50 methanol/water solution (volume basis). The glassy solid contained no free 2-ethyl-2-oxazoline nor any free phenolic —OH groups, as shown by acid-base titration. The product structure was confirmed by nuclear magnetic resonance (NMR) spectroscopy. The product yield was essentially quantitative.

EXAMPLES 2–4

The procedure of Example 1 was followed except that the molar ratios of reactants, amounts of catalysts, temperatures and reaction times were varied. The results are summarized in the following table. The products were again glassy solids in each case. The result from Example 1 is reproduced for the purpose of comparison.

TABLE I

| Ex. | Oxazoline/Bisphenol A Molar Ratio | Zn(OAc)$_2$ · 2H$_2$O (%) | Temp. (°C.) | Time (hr) | Yield (%) | Color |
|---|---|---|---|---|---|---|
| 1 | 2/1 | 0.5 | 170–210 | 5–6 | ~100 | light orange |
| 2 | 2.6/1 | 0.8 | 140–200 | 7 | 98.2 | black |
| 3 | 2.6/1 | 4.0 | 140 | 17 | 98.0 | brown |
| 4 | 2.6/1 | 6.0 | 125 | 12 | 97.5 | yellow |

EXAMPLE 5

A mixture of 426 g (1.0 mole) of the diamide obtained in Example 1 and a solution of 104 g (2.6 moles) of sodium hydroxide dissolved in 416 g of water was purged with nitrogen. The mixture was brought to and held at reflux under a slow nitrogen stream for 120 hours. Titration indicated about a 97 percent conversion of the diamide to diamine. The diamine was isolated from the reaction mixture by extraction with methylene chloride. The methylene chloride/diamine extract was washed twice with water, the water removed via azeotropic distillation, and the solvent then removed. The yield was 86.2 percent, based on theory, and product purity by titration with hydrochloric acid was 98–100 percent.

EXAMPLE 6

Following the method of Example 5, a mixture of 426 g (1.0 mole) of the diamide obtained in Example 1 and a solution of 251 g of 12 normal hydrochloric acid dissolved in 251 g of water was held at reflux until essentially complete hydrolysis was obtained (5 to 7 hours). Samples of this hydrolysis were taken from time to time and analyzed by NMR. These NMR studies also showed a 5 percent loss of aminoethyl groups in 5 hours and a 10 percent loss at 7 hours due to hydrolysis of the arylalkyl ether linkages. The diamine product was recovered by rendering the reaction mixture basic (pH of about 12) with sodium hydroxide, extracting the product with methylene chloride, and working up the extract as per Example 5. The yield was 86.2 percent, based on theory. The compound had a freezing point of −12° C.

EXAMPLE 7

Following the method of Example 1, a mixture of 28.7 g (0.125 mole) of bisphenol A, 37.0 g (0.25 mole) of 2-phenyl-2-oxazoline and 0.5 g of zinc acetate dihydrate was purged with nitrogen and heated to 215° C. under a slow nitrogen stream. The mixture was refluxed at this temperature for about 3.7 hours and cooled. The yield of a tan colored solid with a melting point of 55° C. was 95.3 percent. NMR spectroscopy studies confirmed that 98.8 percent of the product was composed of the diamide with the expected structure.

EXAMPLE 8

Following a method similar to Example 1, a mixture of 272.0 g (0.5 mole) of ar,ar,ar',ar'-tetrabromobisphenol A, 108.9 g (1.1 moles) of 2-ethyl-2-oxazoline and 1.0 g of zinc acetate dihydrate was charged to a one liter glass resin kettle, purged with nitrogen, and heated to 180° C. under a slow nitrogen stream. The mixture was held at 180° C. for 4 hours and cooled. The yield of a brown glassy solid with a melting point of 50° C. was essentially quantitative. NMR spectroscopy studies indicated a 97.5 percent conversion to the diamide predicted by theory. Reaction times in duplicative experiments greater than 8 hours or at higher temperatures produced a darker product.

EXAMPLE 9

Following the method of Example 6, a mixture of 125 g (0.17 mole) of the diamide obtained in Example 8, 42.3 g of 12 normal hydrochloric acid and 42.5 g of water was purged with nitrogen. The mixture was brought to and held at reflux (120°–145° C.) for 9 hours. The yield of the resultant amine hydrochloride salt was 97.2 percent. The salt was taken up in an 80/20 mixture of methanol and methylene chloride, neutralized with 30 percent caustic solution, and diluted with twice the volume of water. The organic phase separated, was isolated and evaporated to dryness. Overall yield was 104 g or 97 percent. NMR spectroscopy studies indicated a purity of the predicted brominated diamine of greater than 98 percent.

EXAMPLE 10

A mixture of 72.9 g (0.708 equivalents of phenolic OH; q=4.26) of a phenol-formaldehyde novolac, 73.6 g (0.74 mole) of 2-ethyl-2-oxazoline and 0.74 g of $SnCl_2$ was charged to a glass resin kettle. The mixture was purged with nitrogen and heated to reflux under a slow nitrogen stream. Refluxing began after 30 minutes at 180° C. The temperature slowly increased to 210° C. within 6 hours. It was held at 210° C. for 4 additional hours. Upon cooling, 132.5 g (or 90 percent yield) of solid was obtained. NMR spectroscopy studies conducted in formic acid indicated one (—$CH_2CH_2NH$-C(O)$CH_2CH_3$) group per methylene bridge, for a conversion of 84 percent.

EXAMPLE 11

50.0 g (0.25 mole) of a bisphenol F novolac (hydroxyl functionality of 2.12) was charged to a 250 cc round-bottomed flask equipped with a magnetic stirrer and reflux condensor. 2.5 g of iron (II) sulfate heptahydrate was added, followed by 55.5 g (0.56 mole) of 2-ethyl-2-oxazoline. This caused an immediate change in color of the reaction mixture from a light green to a dark purple upon stirring. The mixture was heated and refluxing began at a head temperature of 148° C. and a pot temperature of 180° C. The pot temperature then increased quite rapidly to 208° C. The reaction appeared to be essentially complete in 20 minutes but the mixture was held at 208° C. for 2.25 hours. Upon cooling, the pot material solidified to a very dark, brown-black glassy solid. This product was soluble in acetone, chloroform and methanol, but insoluble in hot or cold water.

EXAMPLE 12

The diamine product obtained in Example 5 was tested at various concentrations for its insecticidal, fungicidal and bacteriocidal activity. In the latter test, the compound was diluted in isopropanol or other appropriate solvent, then diluted to the desired concentration in warm melted agar and poured into a petri dish. After the agar solidified, droplets of the test organism were applied to its surface and the plates then incubated at an appropriate temperature for a suitable time.

The compound thus was found to be active at concentrations of about 500 parts per million (ppm) in the control and killing of the following microorganisms: *Psueudomonas aeruginosa, Candida albicans, Trichophton mentagrophytes, Kleb pneumoniae, Aerobacter aerogenes, Candida pelliculosa,* Pseudomonas, *Serratia marcesens, Aspergillus fumig* and others. Similarly the compound was active at lower concentrations ranging from 50–100 ppm on *Staphylococcus aureus, Bacillus subtilis, Pullularia pullulans,* Ceratocystis, *E. Coli* and others. The compound was especially useful in the control and killing of *Salmonella typhosa,* proving effective at concentrations as low as 5 ppm.

As an insecticide, activity against the beet army worm larvae was exhibited at a level of 400 ppm.

As a fungicide, the test consisted of wetting the host plants with an aqueous solution or suspension of the compound, followed by inoculation with the pathogen. The plants were then stored in conditions suitable for infection and development of the pathogens. The compound served as an excellent fungicide for Downey mildew at concentrations of 400 ppm.

EXAMPLE 13

The diamine product obtained in Example 5 (—NH equivalent weight of 78.5) was tested as an epoxy curing agent by blending 7.85 g with 18.7 g of a liquid epoxy resin (in essence, the diglycidyl ether of bisphenol A) having an epoxy equivalent weight of approximately 187 and heating for 2 hours at 100° C. The excellent properties of the cured resin are shown in Table II below.

TABLE II

| Hardener | Initial Temperature (°C.) | HDT[a] | Izod[b] | Gel Time[c] |
|---|---|---|---|---|
| Diamine Product | 25 | 95–101 | 1.3–2.9 | 36 |

[a]Heat Distortion Temperature in °C., as described in American Society of Testing Materials D-648-56.
[b]Notched Izod Impact Strength in ft lbs/inch width of notch, as described in American Society of Testing Materials D-256-56.
[c]Society of Plastics Industry Gel Time in minutes. 500 g reaction mass starting at the initial temperature above.

The viscosity of the diamine product was similar to that of the liquid epoxy resin at temperatures up to 110° C. This facilitated handling and mixing in the curing operations.

The above examples are merely illustrative of our novel compounds, process for preparing same and the utilities of the new compounds. The examples are not, however, to be construed as limiting.

We claim:

1. A process for preparing a compound of the formula

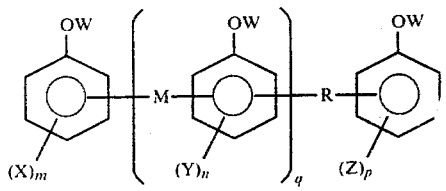

wherein R is a chemical bond, oxygen, sulfur, alkylene or alkylidene; W is hydrogen or a (—CR$_1$R$_2$—CR$_3$R$_4$—NHR$_5$) group with the proviso that at least two W groups are (—CR$_1$R$_2$—CR$_3$R$_4$—NHR$_5$) groups; wherein R$_1$-R$_4$ are each independently hydrogen, lower alkyl or hydroxy-substituted lower alkyl; R$_5$ is a

group, wherein R$_6$ is hydrogen, hydrocarbyl or inertly substituted hydrocarbyl; X, Y and Z are each independently inert substituents; m and p are each independently integers of from zero to four, inclusive; n is an integer of from zero to three, inclusive; q is a number of from zero to about ten; and M is alkylene or alkylidene, comprising reacting by contacting a 2-oxazoline of the formula:

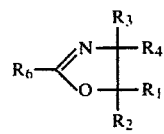

with a polyhydric polyphenol of the formula:

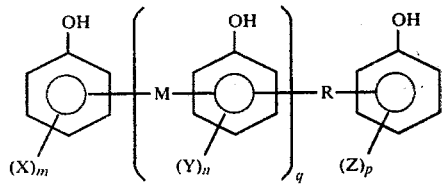

in the presence of a small but catalytic amount of at least tin or one transition metal salt, said transition metal salt catalyst being a salt of a metal in groups 1b, 2b, 6b, 7b and 8 which is included in rows 4 and 5 of the Periodic Table of the Elements, inclusive.

2. The process defined by claim 1 wherein said transition metal salt catalyst is zinc acetate.

3. The process defined by claim 1 wherein said reaction is carried out at a temperature of from about 125° C. to 215° C.

4. The process defined by claim 1 wherein the equivalent ratio of said 2-oxazoline to the hydroxyl equivalents of said polyhydric polyphenol is from about 1:1 to about 1.3:1.

5. The process defined by claim 1 wherein said reaction is carried out in an inert atmosphere.

6. A process for preparing a compound of the formula

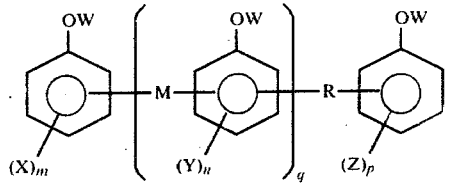

wherein R is a chemical bond, oxygen, sulfur, alkylene or alkylidene; W is hydrogen or a (—CR$_1$R$_2$—CR$_3$R$_4$—NHR$_5$) group with the proviso that at least two W groups are (—CR$_1$R$_2$—CR$_3$R$_4$—NHR$_5$) groups; wherein R$_1$-R$_4$ are each independently hydrogen, lower alkyl or hydroxy-substituted lower alkyl; R$_5$ is hydrogen; X, Y and Z are each independently inert substituents; m and p are each independently integers of from zero to four, inclusive; n is an integer of from zero to three, inclusive; q is a number of from zero to about ten; and M is alkylene or alkylidene, which comprises:

(a) reacting by contacting a 2-oxazoline of the formula:

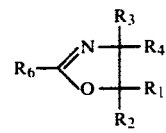

with a polyhydric polyphenol of the formula:

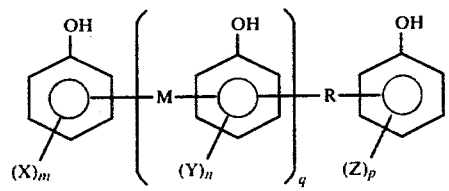

wherein R$_6$ is hydrogen, hydrocarbyl or inertly-substituted hydrocarbyl, and the other substituents are defined above, in the presence of a catalytic amount of at least tin or one transition metal salt, said transition metal salt catalyst being a salt of a metal in groups 1b, 2b, 6b, 7b and 8 which is included in rows 4 and 5 of the Periodic Table of the Elements, inclusive;

(b) reacting product from Step (a) with acid or base to effect hydrolysis, thereby forming a polyamine of the formula:

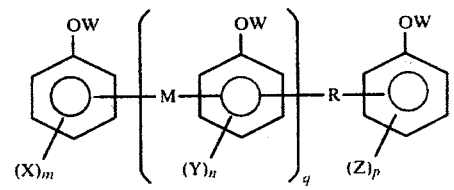

as the free amine or acid salt thereof.

7. The product resulting from the process defined by claim 6.

8. A thermally curable composition comprising an epoxy resin and a cross-linking amount of the polyamine defined by claim 6.

9. The process defined in claim 6, wherein R is isopropylidene.

10. The product resulting from the process defined in claim 9.

11. A thermally curable composition comprising an epoxy resin and a cross-linking amount of the polyamine defined by claim 9.

12. The process defined in claim 6, wherein the 2-oxazoline and polyhydric polyphenol in Step (a) are 2-ethyl-2-oxazoline and Bisphenol A, respectively.

13. The product resulting from the process defined in claim 12.

* * * * *

UNITED STATES PATENT AND TRADEMARK OFFICE
CERTIFICATE OF CORRECTION

PATENT NO. : 4,195,154
DATED : March 25, 1980
INVENTOR(S) : Mark E. Kaiser and Harry A. Smith It is certified that error appears in the above-identified patent and that said Letters Patent are hereby corrected as shown below:

In Col. 2, line 12, delete "indepedently" and insert --independently--.

In Col. 3, line 54, delete "ar" and insert --are--.

In Col. 4, line 32, delete "(2,2-bis(4-hyroxyphenyl)methane)" and insert -- (2,2-bis(4-hydroxyphenyl)methane) --.

In Col. 4, line 36, delete "bisphenols" and insert --biphenols--.

In Col. 4, line 66, delete "technitium" and insert --technetium--.

Signed and Sealed this

Twenty-second Day of July 1980

[SEAL]

Attest:

Attesting Officer

SIDNEY A. DIAMOND

Commissioner of Patents and Trademarks